United States Patent [19]
Lynd et al.

[11] Patent Number: 5,837,506
[45] Date of Patent: Nov. 17, 1998

[54] CONTINUOUS PROCESS FOR MAKING ETHANOL

[75] Inventors: Lee R. Lynd, Meriden, N.H.; Colin R. South, Waltham, Mass.

[73] Assignee: The Trustee of Dartmouth College, Hanover, N.H.

[21] Appl. No.: 916,742

[22] Filed: Aug. 19, 1997

Related U.S. Application Data

[63] Continuation of Ser. No. 439,232, May 11, 1995, abandoned.

[51] Int. Cl.$^6$ .................................................... C12P 7/10
[52] U.S. Cl. ........................ 435/165; 435/161; 435/162; 435/163; 435/170; 435/171
[58] Field of Search .................................. 435/161, 162, 435/163, 165, 170, 171

[56] References Cited

U.S. PATENT DOCUMENTS

| | | | |
|---|---|---|---|
| 4,094,742 | 6/1978 | Bellamy | 195/33 |
| 4,376,163 | 3/1983 | Ehnstrom | 435/162 |
| 4,385,118 | 5/1983 | Muller et al. | 435/162 |
| 4,395,543 | 7/1983 | Wang et al. | 536/56 |
| 4,409,329 | 10/1983 | Silver | 435/105 |
| 4,451,566 | 5/1984 | Spencer | 435/162 |
| 4,640,767 | 2/1987 | Zajic et al. | 208/390 |
| 4,690,903 | 9/1987 | Chen et al. | 435/161 |
| 4,996,150 | 2/1991 | Joung et al. | 435/161 |
| 5,047,332 | 9/1991 | Chahal | 435/42 |
| 5,182,199 | 1/1993 | Hartley | 435/162 |
| 5,258,293 | 11/1993 | Lynd et al. | 435/165 |
| 5,348,871 | 9/1994 | Scott et al. | 435/165 |

OTHER PUBLICATIONS

R.H. Kleijntjens et al., A Continuous Thermophilic Cellulose Fermentation in an Upflow Reactor by a Clostridium Thermocellum–Containing Mixed Culture, *Biotechnology Letters*, vol. 8, No. 9, pp. 667–672, 1986.

Firoz R. Mistry et al., Production of Ethanol by *Clostridium thermosaccharolyticum*: I. Effect of Cell Recycle and Environmental Parameters, *Biotechnology and Bioengineering*, vol. 34, pp. 1295–1304, 1989.

C.R. South et al., Continuous Fermentation of Cellulosic Biomass to Ethanol, *Applied Biochemistry and Biotechnology*, vol. 39, 40, pp. 587–600, 1993.

C.R. South et al., Analysis of Conversion of Particulate biomass to Ethanol in Continuous solids Retaining and Cascade Bioreactors, *Applied Biochemistry and Biotechnology*, vol. 45/46, pp. 467–481, 1994.

Leticia Zertuche et al., A Study of Producing Ethanol from Cellulose Using *Clostridium thermocellum*, *Biotechnology and Bioengineering*, vol. XXIV, pp. 57–68, 1982.

Roychoudhury, P.K. et al., "Enzyme Microb. Technol.," vol. 14(7), pp. 581–585, Jul. 1992.

Chen, S. et al., "Process Biochemistry," vol. 24(6), pp. 204–207, Dec. 1989.

Scott, T.C. et al., "Applied Biochemistry and Biotechnology," vol. 51/52, pp. 537–543, 1995.

*Primary Examiner*—Chhaya D. Sayala
*Attorney, Agent, or Firm*—Lahive & Cockfield, LLP

[57] ABSTRACT

An improved continuous process for producing ethanol from cellulosic materials employs an intermittently agitated, perpetually fed, solids retaining reactor vessel. Cellulosic substrate, catalysts and fermentation agents are introduced into a reaction vessel to form a slurry. The slurry is agitated for a first selected time interval under conditions sufficient to initiate and maintain a fermentation reaction and then allowed to settle during a second selected time interval. At the end of the second selected time interval an ethanol-containing effluent is removed from the vessel. Thereafter, additional cellulosic material, catalysts and fermentation agents are added to the reactor vessel. This operating cycle is repeated virtually perpetually to effect the ethanol production. It can be implemented using a single bioreactor or a cascade of bioreactors.

13 Claims, 2 Drawing Sheets

5,837,506

CONTINUOUS PROCESS FOR MAKING ETHANOL

This application is a continuation application of U.S. Ser. No. 08/439,232, filed on May 11, 1995, now abandoned.

BACKGROUND OF THE INVENTION

This invention relates to a continuous process for making ethanol from cellulosic raw materials. More particularly, it relates to a continuous process for making ethanol which optimizes ethanol production and minimizes inhibition.

Typically the ethanol production process involves the breakdown, or hydrolysis, of cellulose-containing materials, such as wood, into disaccharides such as cellobiose and ultimately monosaccharides, such as glucose and xylose. Microbial agents, including yeasts, then convert the monosaccharides into ethanol in a fermentation reaction which can occur over several days or weeks.

Among the process options for producing ethanol from lignocellulosic substrates (e.g., trees, grasses, and solid wastes) are those known as Direct Microbial Conversion ("DMC") and Simultaneous Saccharification and Fermentation ("SSF"). In the DMC method, a single microbial system both produces cellulase enzymes and produces ethanol as a fermentation product. The SSF method utilizes two microbial systems, one of which produces celullase enzymes and the other of which carries out the fermentation process to produce ethanol.

In known batch processes for producing ethanol, reactants are added to a reaction vessel at the beginning of the production cycle and ethanol product is withdrawn from the vessel at the end of the production cycle, with no intermediate addition of raw materials or withdrawal of product from the vessel. In such batch processes the rate of ethanol production can be limited by the existence of large amounts of hydrolysis products (glucose) and final product (ethanol) and low initial concentrations of microorganisms. In addition, the productivity of batch processes inherently suffers from "down time" during which equipment is cleaned and the bioreactor is recharged. Such rate limitations give rise to a need to use larger bioreactors for a given rate of ethanol production.

A continuous stirred tank reactor (CSTR) process overcomes at least some of the limitations of batch processes. The CSTR process features continuous stirring or agitation of the substrate slurry by, for example, mechanical mixing or liquid recycling. The CSTR process allows optimization and balancing of the hydrolysis and fermentation rates to eliminate the large accumulation of glucose and the resulting inhibition of ethanol production. The CSTR process employs continuous addition of fermentable substrate, catalysts and fermentation agents, and continuous removal of any residual substrate—and product-containing broth. The CSTR process has perpetually high concentrations of microorganisms, much reduced down time compared to batch reactors, generally lower maximum concentrations of potentially inhibitory mono- and disaccharides, but higher ethanol concentration. Thus, the relative merits of batch and CSTR will depend upon the needs and circumstances surrounding a given application.

The use of a continuous solids retaining bioreactor (CSRB) provides further improvements in the production of ethanol. The CSRB improves productivity and yield by providing differential solids retention and thus increasing the concentration of substrate particles in the reactor and increasing the hydrolysis rate. The use of a CSRB increases the overall hydrolysis rate and thus reactor productivity by maximizing the amount of cellulose/enzyme complex in the reactor. The key to efficiency in the CSRB process appears to be the management and control of the cellulose/enzyme complex in the reactor.

U.S. Pat. No. 5,258,293 to Lynd et al., which is incorporated herein by reference, discloses a continuous process for making ethanol that utilizes differential solids retention in a steady state fashion.

A further advancement in the production of ethanol is the use of cascaded CSRBs, in which the output from one CSRB reactor vessel becomes the input feed to the next CSRB reactor vessel. This arrangement overcomes the problem of decreased or limited productivity enhancement with high conversion, as the cascaded reactors achieve higher total conversion for an equal cumulative residence time. However, the solids retention in the later stages is always less than in the early stages as a result of reduced cellulose particle size, because smaller particles require more time to settle. An advantage of the cascaded CSRB system over the single CSRB is that at high conversion, the presence of large amounts of ethanol in a single CSRB inhibits the further production of ethanol, whereas this inhibition is alleviated to some extent in a cascade system because the average concentration of alcohol seen by the reaction is reduced as the reaction proceeds through sequential steady state reactors at increasing ethanol concentration until the final concentration is reached.

It is therefore an object of this invention to provide improved methods for the efficient production of ethanol from cellulosic materials. It is also an object of the invention to enhance the performance of continuous solids retaining bioreactors used in the production of ethanol. Other objects will be apparent upon reading the following disclosure.

SUMMARY OF THE INVENTION

The present invention provides a process for producing ethanol from cellulosic materials. Ethanol production is accomplished according to this invention utilizing an intermittently agitated, perpetually fed, solids retaining bioreactor. This process has surprisingly been found to be an efficient and productive means for ethanol production as hydrolysis products accumulate during fully continuous operation with low mixing intensity. The process of the invention offers the advantages of eliminating accumulation of unutilized sugars while producing an effluent having a composition that is time-invariant. That is, successive intermittently withdrawn aliquots of effluent have the same chemical composition.

The invention, as noted above, uses an intermittently agitated, perpetually fed, solids retaining bioreactor, or to a cascade of such bioreactors. According to the process of the invention cellulosic substrate and catalysts are added to a reaction vessel to form a slurry. The slurry is agitated for a first, selected time interval under conditions sufficient to initiate and maintain a fermentation reaction. The slurry is then allowed to settle for a second selected time interval. Once the second selected time interval expires, ethanol-containing effluent is removed from the reaction vessel. Additional cellulosic substrate, catalysts and fermentation agents can then be added to the reaction vessel. This cycle can be repeated indefinitely.

The process of this invention utilizes differential solids retention. That is, insoluble substrate (solids) have a longer residence time within the reactor than do either the liquid or feed slurry. Differential solids retention is accomplished by withdrawing ethanol-containing liquid effluent from the reaction vessel after the settling period (i.e., the second selected time interval). In this way solids are allowed to settle and remain in the reaction vessel.

Increased solids retention, with consequent improved ethanol production efficiency and productivity, is attainable in a perpetual, continuous process for producing ethanol. This process comprises the periodic (or intermittent) agitation of the reactants, allowing the reactant suspension to settle for a selected time period, and then withdrawing products and adding reactants. This sequence of process steps eliminates the accumulation of hydrolysis products and provides consistently higher productivity.

The process further comprises separating the ethanol-containing effluent into a residual component which can include solid cellulosic substrate, catalysts and fermentation agents, and an ethanol-enriched component (which is ethanol-enriched with respect to the residual component). If desired, agitation can be effected by reintroducing at least a portion of effluent, preferably the residual component, into the reaction vessel. Agitation can also be effected by mechanical mixing.

Additional advantages of this invention include, for example, the ability to use a wider variety of fermentable substrates, including waste products that might otherwise have been unusable; the ability to increase the productivity of ethanol-producing reactors and thus increase yield; and the ability to decrease the costs of ethanol production, possibly leading to an increased use of ethanol as an alternative fuel source.

BRIEF DESCRIPTION OF THE DRAWINGS

For a fuller understanding of the nature and objects of the invention, reference should be made to the following detailed description and the accompanying drawings, in which.

DETAILED DESCRIPTION OF THE INVENTION

The process of the present invention employs an intermittently agitated, perpetually fed, solids retaining bioreactor to produce ethanol from cellulosic substrates. The slurry within the reaction vessel is intermittently agitated and allowed to settle before the removal of solids-rarefied ethanol-containing effluent and the addition of unreacted feed. The result of this intermittent agitation and settling is a significant increase in the production of ethanol and the elimination of inhibition, presumably due to accumulated hydrolysis products.

Figure 1:
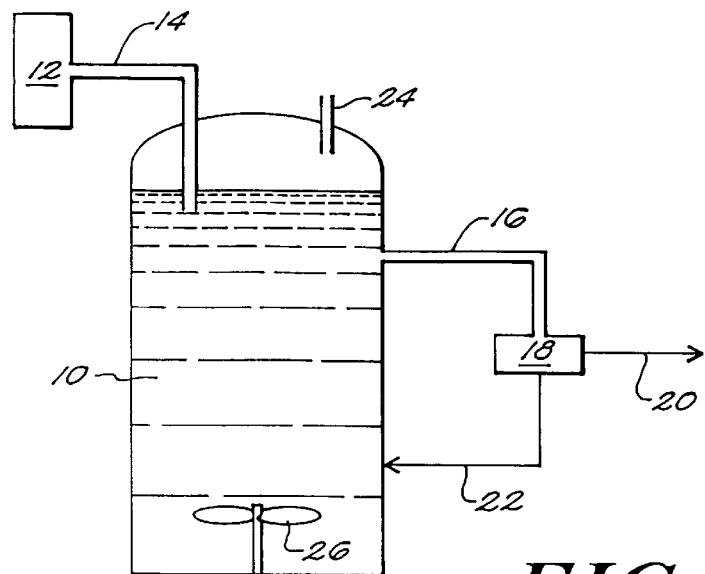
FIG. 1 is a schematic diagram of a reaction vessel useful for carrying out the present invention.

FIG. 1 illustrates a bioreactor 10 of the type useful in practicing the process of the invention. Reservoir 12 houses a slurry of cellulosic substrate material which is fed into the bioreactor 10 through conduit 14. The bioreactor 10 also includes an effluent conduit 16 which exits the bioreactor, preferably at an upper portion thereof. Effluent conduit 16 can be used to withdraw ethanol containing liquid effluent from the bioreactor to station 18. At station 18 the effluent can be separated into an ethanol enriched stream 20 and a residual stream 22 which, in one embodiment, can be recycled to bioreactor 10. Station 18 can also perform effluent monitoring and processing functions where pH is monitored and adjusted, if necessary. Preferably, the bioreactor 10 also includes a vent 24 from which fermentation gases may be withdrawn from the bioreactor. In addition, the bioreactor may also include a mechanical mixing device 26.

Ethanol enriched stream 20 can be directed to further processing stations or, if a cascade of bioreactors is to be used, it can be directed to downstream bioreactors.

A bleed stream (not shown) can be used periodically to remove from the bioreactor any inerts that may accumulate at the bottom of the bioreactor.

It is not necessary that residual stream 22 be recycled to the bioreactor. However, if such recycling is utilized, one of ordinary skill in the art will appreciate that the positioning of conduit 14 and residual stream 22 can be varied. For example, conduit 14 may be repositioned to deposit additional slurry to a bottom portion of bioreactor 10. Also, liquids in residual stream 22 can be directed to top, bottom or intermediate regions of the bioreactor 10.

In a preferred embodiment, predetermined quantities of a cellulosic substrate material, an enzyme for hydrolyzing the cellulose, and a growth medium to sustain the viability of the microbial agent, are added to the bioreactor 10 from reservoir 12 to form a slurry. The raw materials in the bioreactor are then reacted at approximately 37° C. to promote and maintain hydrolysis of the cellulosic substrate and fermentation of the resulting hydrolysis products.

It is understood that the operating strategy of the invention is applicable to use with a cascade of bioreactors.

The substrate used in practicing the method of the invention is generally categorized as a lignocellulosic raw material. Exemplary classes of lignocellulosic raw materials which may be used as a substrate material include woody biomass, herbaceous biomass (e.g., forage grasses e.g., herbaceous energy crops), agricultural residue, and waste material (e.g., waste paper sludge, and municipal solid waste). Exemplary woody biomass materials include hardwoods such as poplar, oak, maple, and birch. A preferred pretreatment process for such hardwoods is dilute-acid hydrolysis.

The size range of the substrate material varies widely and depends upon the type of substrate material used as well as the requirements and needs of a given process. Depending on the pretreatment process employed, the size of the substrate particles, prior to pretreatment, ranges from less than a millimeter to inches in diameter, and need only be of a size that is reactive. Most preferably, the particle size of the substrate material after pretreatment is in the range of about 0.5 to 12 millimeters, and most preferably about 2 millimeters.

The cellulosic material is preferably pretreated in order to render the fermentable material accessible to enzymes. Examples of such pretreatment processes include dilute-acid hydrolysis, steam explosion, and ammonia fiber explosion. The cellulosic substrate can be pretreated by heating the substrate in, for example, a dilute aqueous sulfuric acid solution at a temperature of at least 160° for up to several minutes. The pretreated cellulosic substrate can then be sterilized, if desired, to prevent growth of other microorganisms during the fermentation reaction.

The enzymes used in the method of this invention include, for example, Genencor CL cellulase available from Genencor Inc. (San Francisco, Calif.) and Novozyme 188

β-glucosidase available from NOVO Laboratories Inc. (Wilton, Conn.). The addition of β-glucosidase to the cellulase increases the specific activity of the cellulase solution by reducing the accumulation of cellobiose and preventing or minimizing the resulting inhibition of glucose production.

A variety of microorganisms are known to be useful for the conversion of organic material to ethanol. One of ordinary skill in the art can readily select a desirable microorganism(s) for use in the method of the present invention, whether the DMC process or the SSF process options are to be used. One example of a preferred microorganism useful in converting organic matter to ethanol by way of the DMC process is *Clostridium thermocellum*. Other examples of suitable microorganisms which may be used with the DMC process option include *Fusarium oxysporum* and *C. cellulyticum*. In addition, such organisms can be used in co-culture with *C. thermosaccharolyticum* or similar pentose-utilizing organisms such as *C. thermohydrosulfuricum* and *Thermoanaerobacter ethanolicus*.

Examples of preferred microorganisms which may be used in the practice of the method of the present invention according to the SSF technique are *Trichoderma reesei* (for producing cellulase enzymes) and *Saccharomyces cerevisiae* (which produces ethanol). Other examples of cellulase-producing organisms which may be used with the SSF process option include *Acidothermus cellulyticus* and *Trichoderma koningii*, while an alternative ethanol-producing organism which may be used with the SSF process option is *Zymomonas mobiles*. One skilled in the art can readily identify a variety of additional suitable microbial systems which may be used with the SSF process option.

A variety of suitable growth media are well known in the art and can be selected by one having ordinary skill in the art, depending upon which microorganism(s) is used. Generally, it is required that a suitable growth medium be able to provide the chemical components necessary to maintain metabolic activity and to allow cell growth. One effective growth medium contains the following components per liter of distilled water:

| Component | Amount |
| --- | --- |
| Yeast Extract | 10 g/L |
| Peptone | 20 g/L |

The medium noted above is set forth by way of example only. It is expected that other suitable growth media may be useful for practicing the method of the invention as well.

Figure 2:
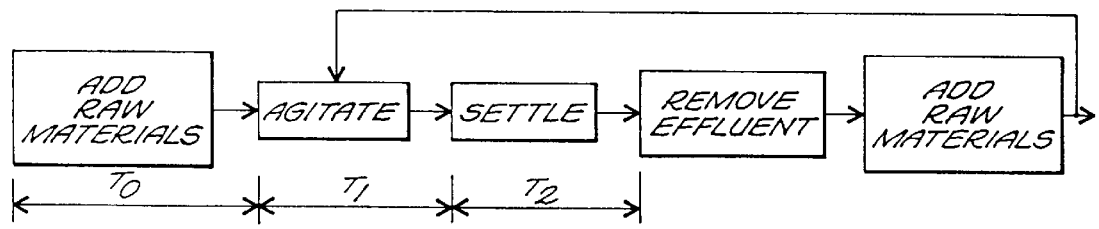
FIG. 2 is a schematic diagram of the method of the present invention.
Figure 3:
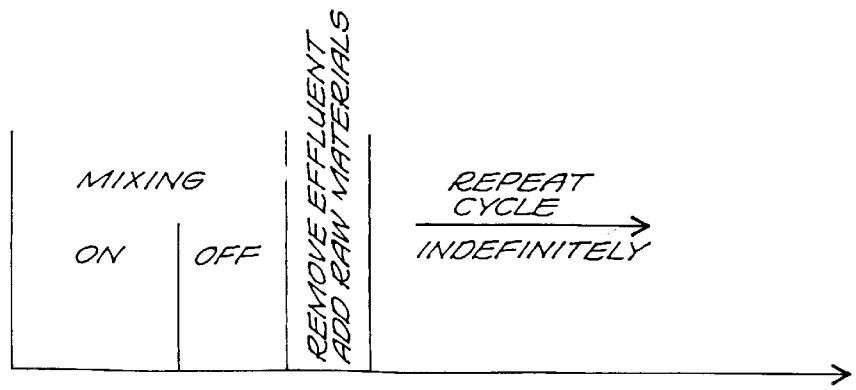
FIG. 3 illustrates the process sequences of the present invention.

FIGS. 2 and 3 illustrate the process of the invention in which raw materials necessary for the ethanol production are first added to a reaction vessel to form a slurry. The slurry is agitated for a first selected time period so that the solid cellulosic substrate particles are uniformly dispersed within the reactor vessel to ensure that they are exposed to cellulase. Agitation can be accomplished using a variety of devices, including mechanical devices such as vortex mixers and gate stirrers. A preferred agitation speed is about 100 rpm, although the invention can also be practiced using higher or lower agitation speeds. Agitation can also be accomplished by recycling liquid back to the bioreactor, as discussed below in more detail.

Agitation proceeds for a first selected time period ($T_1$), and then is ceased. The duration of the first selected time period ($T_1$) can vary widely from about 30 minutes to several hours. A more preferred duration of period $T_1$ is from about 30 minutes to about 3 hours. Following this agitation period ($T_1$), the slurry is allowed then to settle for a second selected time period, or settling period ($T_2$). During this settling period ($T_2$) no product is withdrawn from, and no reactants are added to the reactor. The second selected time period ($T_2$) can be virtually any length of time that is sufficient to allow settling of the insoluble substrate. Generally, the second selected time period ($T_2$) is less than the agitation period ($T_1$). The optimum settling period will be determined in part by the properties and particle size of the cellulosic substrate material. The settling period is preferably shorter than the agitation period and most preferably is only long enough to permit settling of a significant fraction (e.g., about 50%) of the solids in the slurry. A preferred settling period is from about 2 to 60 minutes, and more preferably from about 5 to 45 minutes.

Following the completion of the settling period ($T_2$), ethanol-containing effluent can be withdrawn from the reactor vessel. Preferably, the ethanol-containing effluent is removed from a top portion of the reactor vessel, since the top portion of the reactor vessel should be relatively free of suspended solids after the settling period and before the next agitation period. The ethanol-containing effluent can then be separated into an ethanol-enriched component and a residual component. The ethanol enriched component can then be further processed and distilled to yield ethanol suitable for the desired applications.

The residual component of the effluent typically contains solid, non-hydrolyzed or non-hydrolyzable substrate material, enzymes and microbial agents. The residual component can be recycled to the slurry within the bioreactor. In one embodiment of the invention, the addition of such reconstituted residual effluent component to the slurry in the bioreactor can be performed during the first selected time period ($T_1$) to effect agitation of the slurry. This recycling can be done as the sole means of agitation or to supplement mechanical agitation with the bioreactor. Alternatively, the residual effluent can be added continuously to the bioreactor.

Following the settling period, and before further agitation, additional cellulosic substrate, enzymes, and growth medium are normally added to the reactor. Preferably these raw materials are added after the ethanol-containing effluent is removed to avoid contamination of the ethanol-containing effluent with unreacted raw materials, enzymes or microbial agents and achieve maximum solids retention in the reactor.

This processing sequence can be repeated any number of times to effect a virtually perpetual ethanol production process.

One feature of the invention that is believed to contribute to desirable efficiency and ethanol production is the differential retention of solids. Differential solids retention can be accomplished by withdrawing ethanol containing liquid effluent from a top portion of the bioreactor after the settling period of the operating cycle such that the solids concentration in the withdrawn effluent is less than that corresponding to the total reactor solids inventory divided by the volume of slurry in the reactor. Following the mixing cycle the entire liquid phase has an essentially consistent composition.

Among the benefits of the process of the invention is a novel operating strategy and implementation of solids retention in a cascade of bioreactors. Conventional operating modes suffer significant process limitations, most notably high amounts of unutilized sugars when used in conjunction with CSRB. The present operating strategy utilizes intermittent feeding and effluent withdrawal for a perpetually fed, solids retaining reactor which circumvents the limitations of conventional operating modes.

The following non-limiting examples serve to further define the invention and advantages thereof.

EXAMPLE 1

A fermentor of 1.24 L fitted with a bottom mounted stirrer was autoclaved to ensure sterility. After autoclaving the fermentor was filled to 10% full volume with medium (as described above). The fermentor was then brought to temperature (37° C. by the fermentor water jacket) and an innocullum of biocatalyst (*Saccharomyces cerevisiae* which had been grown overnight on a 10 g/L yeast extract, 20 g/L peptone, 20 g/L glucose solution) equal to 10% of the full volume of the reactor was aseptically added. This innocullum entered the rector through a sterile Luer lock fitting. Following inoculation, continuous feeding of the reactor commenced using both the cellulosic substrate (microcrystalline cellulose (AVICEL) PH-105 obtained from FMC Corp. of Newark, Del.) and the cellulase enzyme for SSF. At all times, except as noted below, during the feeding cycle the reactor was stirred using a gate stirrer at 100 rpm.

Feeding of the medium (which had been pH adjusted to 4.5 using sulfuric acid) then commenced in the following manner. The reactor was fed intermittently at such a frequency that the interval between feeding (3 hours) was small compared to the hydraulic residence time of the reactor (18–72 hours). Prior to addition of substrate the solids within the reactor were allowed to settle by stopping the stirring system. After the solids in the reactor had settled (typically 30–60 minutes) the reactor was fed using a fixed volume sample of substrate (8 mL) from a slurry sampling system (Bristol Equipment Company, IL). Substrate entered the reactor through a draft tube which was immersed below the liquid in the reactor. During the time of substrate addition cellulase (Genencor Cytolase CL) was also being added to the reactor draft tube. The input of this fresh material resulted in the overflow from the reactor of liquid and reacted solids through a top level overflow. To aid in the expulsion of liquid and spent substrate from the reactor a short (0.5 sec) burst of nitrogen was used to purge the feed line and reactor. This nitrogen passed out of the reactor with the effluent stream.

Temperature of the reactor was maintained at 37° C. by the use of a recirculation water bath. The pH of the reactor was held at 4.5 by adjustment of the feed substrate pH slurry prior to addition to the reactor.

During fermentation the concentrations of products and residual substrate were measured. After measuring the concentration of unreacted substrate remaining in the reactor and the amount of fermentation products it is possible to establish the extent of solids retention achieved.

From time 0 to time 120 hours the system was operated with continuous stirring at 30 rpm with intermittent feeding at regular intervals. From time 120 hours to 160 hours the system was operated in a batch mode at an agitation speed of 30 rpm. From time 160 hours to 190 hours the system was again operated with intermittent feeding at an agitation speed of 30 rpm. From time 190 hours through the end of the experiment at 360 hours the system was operated according to the processing cycle of the present invention. This processing cycle utilized a MIX-ON period of 60 minutes with a MIX-OFF period of 10 minutes. Agitation speed during the MIX-ON period was 100 rpm.

Figure 4:
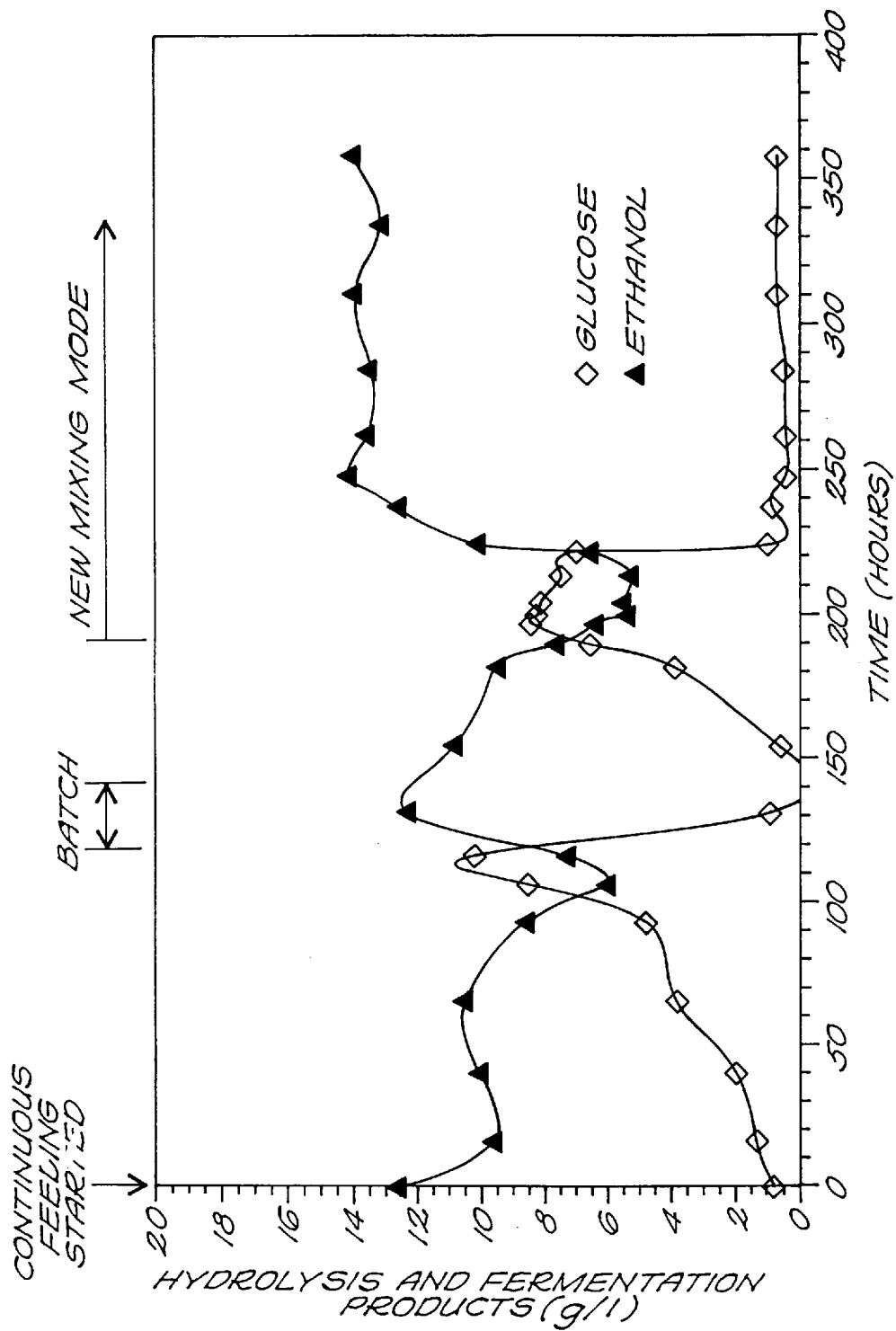
FIG. 4 is a graph illustrating ethanol production characteristics achieved by the present invention.

The data obtained are illustrated in FIG. 4. These data indicate that from time 0 to 120 hours, and from time 160 to 190 hours, using an agitation speed of 30 rpm, the glucose concentration increased to high levels while ethanol concentration decreased. The presence of elevated glucose levels is an indication of inhibition of the fermentation rate (by yeast) to an extent that fermentation becomes rate-limiting. From time 120 to 160 hours, operating in a batch mode at 30 rpm, a rapid decline in glucose concentration and an increase in ethanol concentration was observed. From time 190 to 360 hours, using the processing cycle of the present invention, glucose levels are observed to be low while ethanol concentration is high, indicating that this processing cycle is effective to eliminate the inhibitory effects observed with continuous low-intensity (30 rpm) mixing conditions. Moreover, using this method described, it was possible to achieve solids retention between 2.2 and 2.6 times the liquid residence time when using Avicel as a substrate.

EXAMPLE 2

Tables 1, 2 and 3 illustrate data obtained in an experiment conducted using reactants similar to those used in Example 1. Here, performance data were obtained using (1) a pretreated wood-fed, continuously mixed reactor with agitation speeds of 30 and 60 rpm; (2) a pretreated wood-fed reactor using the cyclical operating strategy of the present invention (60 minutes MIX-ON, 10 minute MIX-OFF); and (3) an Avicel-fed reactor using the present cyclical operating strategy (60 minutes MIX-ON, 10 minutes MIX-OFF). The Avicel-fed reactor utilized microcrystalline cellulose (AVICEL PH-105) obtained from FMC Corp., of Newark, Del. To obtain pretreated wood, wood chips (such as Poplar) were pretreated in a dilute (0.45%) sulfuric acid solution at 170° C. for 10 minutes and then washed to remove any soluble pretreatment products. The cellulosic substrates were autoclaved in a 40 L stainless steel carboy containing a mechanical agitator bar. A separate solution containing 100 g/l yeast extract and 200 g/l peptone was prepared and these solutions were combined after sterilization to yield a feed slurry having the following composition

| | |
|---|---|
| Cellulose from substrate* | 50.0 g |
| Yeast extract | 10.0 g |
| Peptone | 20 0 g |

*The cellulosic substrate may be either AVICEL or pretreated wood.

The feed slurry was mechanically agitated so that it was uniformly mixed.

Results were compared in terms of the time required to reach a given conversion and the ratio of productivity (substrate used/reactor volume and reaction time) in a perpetually fed solids retaining reactor according to the present invention relative to a conventional batch reactor and a CSRB reactor. These results are shown in Tables 1, 2 and 3.

TABLE 1

Comparison of Conversion in Batch and CSRB Reactors

| Substrate | Reactor Configuration | Conversation (%) | Batch | CSRB | Productivity increase (%) | Glucose conc (g/l) |
|---|---|---|---|---|---|---|
| Pretreated Wood | well Mixed 60 rpm | 21 | 0.6 | 1.2 | Negative | <1 |
| | well Mixed 60 rpm | 31 | 1.1 | 2.0 | Negative | <1 |
| | well Mixed 30 rpm | 34 | 1.3 | 1.2 | 8 | 6.5 |

TABLE 1-continued

Comparison of Conversion in Batch and CSRB Reactors

| Substrate | Reactor Configuration | Conversation (%) | Batch | CSRB | Productivity increase (%) | Glucose conc (g/l) |
|---|---|---|---|---|---|---|
| | well Mixed 30 rpm | 41 | 2.1 | 2.0 | 5 | 3.0 |

TABLE 2

Comparison of Conversion for Batch Reactors and Current Process for Pretreated Wood

| Residence time (Days) | Cellulase loading (µ/g cellulose) | Conversion (%) | Time in Batch to reach same conversion (Days) | Differential solids retention time | Number of data points at steady state | Standard deviation (% conversion) | Reactor [solids] (g/L) | Productivity increase †Batch\|X τCSRB |
|---|---|---|---|---|---|---|---|---|
| 2.53 | 15.6 | 74.1 | 3.2 | 2.75 | 7 | 6.2 | 53.8 | 1.26 |
| 2.94 | 11.9 | 66.8 | 4.3 | — | 8 | 4.0 | — | 1.46 |
| 3.02 | 5.57 | 51.6 | 4.4 | 1.41 | 7 | 4.7 | 65.1 | 1.46 |
| 4.67 | 13.3 | 73.1 | 3.6 | 0.99 | 3 | 5.9 | 54.3 | 0.77 |

TABLE 3

Comparison of Conversion for Batches Reactor and Current Process for AVICEL-fed Reactor

| Residence time (Days) | Cellulase loading (µ/g cellulose) | Conversion (%) | Time in Batch to reach same conversion (Days) | Differential solids retention time | Number of data points at steady state | Standard deviation (% conversion) | Reactor [solids] (g/L) | Productivity increase †Batch\|X τCSRB |
|---|---|---|---|---|---|---|---|---|
| 0.75 | 17.7 | 55.9 | 1.66 | — | 8 | 1.6 | — | 2.22 |
| 1.05 | 20.4 | 54.1 | 1.43 | 2.46 | 7 | 4.0 | 58.1 | 1.36 |
| 1.32 | 2.9 | 25.8 | 2.14 | 2.49 | 5 | 2.3 | 76.5 | 1.62 |
| 1.43 | 6.4 | 48.6 | 2.98 | — | 8 | 8.5 | — | 2.08 |
| 1.45 | 4.7 | 41.8 | 3.04 | 2.40 | 8 | 2.6 | 75.5 | 2.60 |
| 1.82 | 1.6 | 26.1 | 3.75 | — | 4 | 2.9 | — | 2.06 |
| 2.00 | 17.0 | 69.0 | 2.61 | 2.54 | 3 | 6.7 | 51.8 | 1.31 |
| 2.05 | 3.9 | 49.2 | 4.62 | 2.20 | 5 | 2.8 | 60.7 | 2.25 |
| 2.07 | 4.23 | 50.6 | 4.50 | 2.28 | 6 | 6.0 | 63.5 | 2.17 |
| 2.44 | 3.4 | 51.0 | 5.56 | — | 2 | 3.8 | — | 2.27 |
| 2.44 | 10.7 | 65.0 | 3.29 | 2.23 | 3 | 2.7 | 47.3 | 1.35 |
| 2.75 | 5.8 | 62.7 | 4.98 | — | 4 | 3.7 | — | 1.81 |
| 2.77 | 17.0 | 66.8 | 2.45 | 2.45 | 4 | 3.1 | 48.8 | 0.88 |
| 3.28 | 14.2 | 76.7 | 3.83 | 2.38 | 7 | 7.5 | 41.2 | 1.17 |
| 3.31 | 11.9 | 72.0 | 3.75 | 2.55 | 3 | 3.4 | 45.2 | 1.13 |
| 4.12 | 20.8 | 77.1 | 2.94 | 2.35 | 3 | 5.6 | 30.8 | 0.71 |

†For those points which the differential solids retention was not measured the average solids retention of 2.4x the hydraulic residence time was used for modeling purposes.

The data of Table 1 indicate that a 60 rpm agitation speed requires a longer reaction time for the solids retaining reactor and thus yields a negative productivity ratio. The use of a 30 rpm agitation speed shows a modest productivity increase (in terms of substrate conversion), but with high glucose concentrations, indicative of inhibition. Tables 2 and 3 illustrate that the solids retaining reactor using the process of the present invention, when fed with either pretreated wood or Avicel, achieves a higher substrate conversion productivity than batch processes while also yielding a low glucose concentration in the effluent.

It is to be understood that various modifications can be made in the method of the invention without departing from the scope of the invention. For example, the fermentation reaction may be run using types of organisms which are not specifically disclosed herein. In addition, while the general design of a suitable bioreactor is provided herein, various modifications and refinements of the bioreactor can be made without departing from the scope of the invention.

All references and publications cited herein are expressly incorporated by reference herein.

What is claimed is:

1. A method for producing ethanol from a cellulosic substrate, comprising the steps of a) providing within a reaction vessel, a reaction mixture in the form of a slurry comprising cellulosic substrate, catalysts and fermentation agents;

b) agitating the reaction mixture for a first selected time interval, wherein the reaction mixture is reacted under conditions sufficient to initiate and maintain a fermentation reaction;

c) ceasing agitation of the reaction mixture for a sufficient period of time to permit insoluble substrate of the reaction mixture to settle during a second selected time interval, thereby forming an ethanol containing effluent layer substantially free of suspended solids and a residual solids layer;

d) removing from the reaction vessel the ethanol-containing effluent upon expiration of the second selected time interval, and before any further agitation;

e) adding a second reaction mixture, comprising the components of the reaction mixture of step a), to the reaction vessel which contains the residual solids; and f) repeating steps (b) through (e) to maintain a continuous fermentation reaction.

2. The method of claim 1 further comprising, after step d), the step of separating the ethanol-containing effluent into an ethanol-rich component and a residual component, which residual component comprises solid cellulosic substrate, catalysts and fermentation agents.

3. The method of claim 2 wherein the slurry is agitated by reintroducing at least a portion of the ethanol-containing effluent to the slurry in the reaction vessel.

4. The method of claim 1 wherein the cellulosic substrate comprises woody biomass herbaceous energy crops, and agricultural residue.

5. The method of claim 1 wherein the ethanol-containing effluent is removed from the top portion of the reaction vessel.

6. The method of claim 1 wherein the slurry is agitated by mechanical mixing.

7. The method of claim 1 wherein the fermentation agents comprise yeasts.

8. The method of claim 1 wherein the catalysts comprise enzymes, selected from the group consisting of cellulase and β-glucosidase.

9. The method of claim 1 wherein the first selected time interval is longer than the second time interval.

10. The method of claim 1 wherein the first selected time interval is in the range of about 30 minutes to 3 hours.

11. The method of claim 1 wherein the second selected time interval ranges from about two minutes to sixty minutes.

12. The method of claim 1 being carried out using a perpetually fed, solids-retaining bioreactor.

13. The method of claim 1 being carried out using a cascade of reaction vessels in which the effluent from upstream reaction vessels is directed to downstream reaction vessels.

* * * * *